US006844369B2

(12) United States Patent
Ninkov (10) Patent No.: US 6,844,369 B2
(45) Date of Patent: Jan. 18, 2005

(54) PESTICIDAL COMPOUNDS AND COMPOSITIONS

(75) Inventor: Dusan Ninkov, Orange City, IA (US)

(73) Assignee: Van Beek Global, LLC, Orange City, IA (US)

( * ) Notice: Subject to any disclaimer, the term of this patent is extended or adjusted under 35 U.S.C. 154(b) by 0 days.

(21) Appl. No.: 10/056,593

(22) Filed: Jan. 23, 2002

(65) Prior Publication Data

US 2002/0156135 A1 Oct. 24, 2002

Related U.S. Application Data

(60) Provisional application No. 60/263,656, filed on Jan. 23, 2001.

(51) Int. Cl.$^7$ ......................... A61K 33/24; A61K 33/34; A61K 35/78
(52) U.S. Cl. ....................... 514/731; 424/405; 424/617; 424/624; 424/641; 424/654; 424/725; 514/783
(58) Field of Search ................................ 514/731, 783, 514/729; 424/617, 641, 624, 654, 405, 725, 745, 630, 408

(56) References Cited

U.S. PATENT DOCUMENTS

| 3,692,916 | A | | 9/1972 | LaBarbera |
| 3,966,779 | A | | 6/1976 | Satzinger et al. |
| 4,380,506 | A | | 4/1983 | Kimura et al. |
| 5,439,690 | A | | 8/1995 | Knight |
| 5,591,435 | A | * | 1/1997 | Vaccarello-Dunkel et al. ...................... 424/740 |
| 5,693,344 | A | | 12/1997 | Knight et al. |
| 5,955,086 | A | | 9/1999 | DeLuca et al. |
| 6,004,569 | A | | 12/1999 | Bessette et al. |
| 6,114,384 | A | | 9/2000 | Bessette et al. |
| 6,183,767 | B1 | | 2/2001 | Bessette et al. |
| 6,231,865 | B1 | | 5/2001 | Hsu et al. |
| 6,322,825 | B1 | * | 11/2001 | Ninkov ...................... 424/745 |
| 6,329,433 | B1 | | 12/2001 | Bessette et al. |
| 6,331,572 | B1 | | 12/2001 | Bessette et al. |
| 6,333,360 | B1 | | 12/2001 | Bessette et al. |
| 6,340,710 | B1 | | 1/2002 | Bessette et al. |

FOREIGN PATENT DOCUMENTS

| JP | 53-66420 | | 6/1978 |
| JP | 04352702 | | 7/1992 |
| JP | 10-109906 | * | 4/1998 |
| WO | WO 98/27261 | | 6/1998 |
| WO | WO 00/00166 | | 1/2000 |
| WO | WO 00/18365 | | 4/2000 |
| WO | WO 00/23040 | | 4/2000 |
| WO | WO 00/78276 A1 | | 12/2000 |

OTHER PUBLICATIONS

Computer Document esp@cenet WO 0118201 Bessette et al Pesticidal Activity of Plant Essential Oils and their Constituents, Mar. 15, 2001.*
Ondarza, M. and Sanchez, A., "Steam Distillation and Supercritical Fluid Extraction of Some Mexican Spices," Chromatographia, vol. 30, No. 1/2, pp. 16–18, (Jul. 1990).
The Merck Index, an encyclopedia of chemicals, drugs, and biologicals, Twelfth Edition, pp. 308 and 1604, (1996).
Brickett, L.A., et al., "Comparison of methods used to inhibit bacterial activity in sulfide ore bioleaching studies," Hydrometallurgy 39, pp. 293–305 (1995).
Gomez, E., et al., "Silver–catalysed bioleaching of a chalcopyrite concentrate with mixed cultures of moderately thermophilic microorganisms," Hydrometallurgy 51, pp. 37–46 (1999).
Kosturiak, Adam, et al., "Fungicidal spray mixture," XP–002197096, 6001 Chemical Abstracts, vol. 122, No. 71, Mar. 13, 1995.

* cited by examiner

Primary Examiner—Herbert J. Lilling
(74) Attorney, Agent, or Firm—McKee, Voorhees & Sease, P.L.C.

(57) ABSTRACT

The invention includes a pesticidal compound comprising at least one organic phenolic compound and at least one salt comprising a divalent cation. Preferably, the organic phenolic compound is chosen from Carvacrol, thymol or combinations thereof; and is derived from a natural source, preferably extracted from a member of the family Labiatae or Verbenacea. Preferably the divalent cation is a transition metal salt and more preferably is zinc chloride or zinc sulfate. The invention also includes methods of eradicating, repelling or preventing infestations of pests, including such pests as insects, mites, ova, fungus, or parasites. The methods comprise the steps of preparing a pesticidal compound, combining it with a carrier, and applying it to the affected area.

25 Claims, 4 Drawing Sheets

PESTICIDAL COMPOUNDS AND COMPOSITIONS

This application claims priority to U.S. Provisional Application No. 60/263,656, filed Jan. 23, 2001 entitled COMPOSITION FOR USE AS A PESTICIDE, the disclosure of which is incorporated herein by reference.

FIELD OF THE INVENTION

The invention relates generally to pesticidal compositions that include organic phenolic compounds, and more specifically to pesticidal compositions that include organic phenolic compounds from oil extracts from plants from the *Labiatae* and *Verbenacea* family and a transition metal ion.

BACKGROUND

Pesticides or pesticidal methods, such as insecticides, are generally used to increase food production, decrease the amount of disease carrying pests, and limit human contact with such pests. Currently, the primary method of controlling such pests is through the application of pesticides containing synthetic chemical compounds. Not only are such chemicals becoming less effective at controlling and/or killing the pests, but they can also cause undesirable effects on both the environment and humans.

Initially many of the synthetic chemicals utilized as pesticides were very effective in controlling and/or killing the pests. However, after extensive usage the pests eventually build up a tolerance or resistance to some such chemicals. Once one chemical loses its utility, other synthetic chemicals, that the pests have not yet developed a tolerance for, are used. This cycle can result in a very large number of synthetic chemicals being released, largely unchecked, into the environment. The interaction of any synthetic chemical, let alone a number of such chemicals with the environment always comes with unexpected consequences.

The non-selective way in which synthetic chemicals control pests also makes them undesirable. The chemicals can often have unexpected and serious detrimental effects on desirable insects or animals as well as the pest insect or animal.

The chemicals can also contaminate areas in which humans have significant contact and cause serious effects on human health. Because of the large number of such synthetic chemicals in the environment, the interaction of such chemicals is inevitable. Often, the combined effect, often called the synergistic effect, of such chemicals can greatly outweigh their singular effects.

Furthermore, synthetic chemicals can often persist in the environment almost indefinitely. These concerns, and others, have lead the United States Environmental Protection Agency (EPA) to regulate and even ban a number of synthetic chemicals used as pesticides.

Because of the often detrimental effects of synthetic chemical pesticides and the EPA's regulatory ban of some such chemicals, a number of alternatives to synthetic chemical pesticides have been proposed and researched.

One such alternative is the use of biological organisms to control the undesired pests. Although this approach has had some significant advances and triumphs, concerns regarding the organism that is being released to control the pest will always remain. Another alternative that is seeing an increased level of interest, is the use of natural pesticides. Natural pesticides are compounds that exist in nature (e.g. in plants, animals, or other insects) and have properties that allow them to be used as is, combined, or modified to be used as pesticides.

An example of a natural pesticide is disclosed in U.S. Pat. No. 6,004,569 (Bessette et al.). Bessette et al. discloses a formulation and method to kill invertebrates, especially insects, arachnids and larvae. The disclosed formulation includes a chemical compound having a six membered carbon ring having substituted thereon at least one oxygenated functional group. Bessette further indicates the formulation is a chemical component of a plant essential oil.

U.S. Pat. No. 6,231,865 (Hsu et al.) is another example of a natural pesticide. Hsu et al. discloses a composition that includes garlic oil or extract with essential oils. The disclosed formulations are said to have a synergistic effect which significantly increases the known qualities of garlic oil.

Although natural pesticides have previously been utilized, there still remains a need for effective natural pesticides that do not have the undesirable effects often exhibited by synthetic chemical pesticides.

SUMMARY OF THE INVENTION

This invention provides pesticidal compositions that include oil extract from plants from the *Labiatae* and *Verbenacea* family and at least one transition metal ion. In particular, the compositions can be formulated by combining extracts of an essential oil with transition metal salts.

Suitable plants from the *Labiatae* and *Verbenacea* family include, but are not limited to, *Ocimum* spp., *Saturea* spp., *Monarda* spp, *Origanum* spp, *Thymus* spp., *Mentha* spp., *Nepeta* spp., *Teucrium gnaphalodes, Teucrium polium, Teucrim divaricatum, Teucrim kotschyanum, Micromeria myrifolia, Calamintha nepeta, Rosmarinus officinalis, Myrtus communis, Acinos suaveolens, Dictamnus albus, Micromeria fruticosa, Cunila origanoides, Mosla Japonoica Maxymowitz, Pycnanthemum nudum, Micromeria Juliana, Piper betel, Trachyspermum ammi* and *Lippia graveolens*. In a preferred composition, the plant is *Nepeta racemosa* or *Nepeta Cataria*.

Examples of suitable transition metal salts include zinc chloride, copper chloride, iron chloride, zinc hydroxide, copper hydroxide, and iron hydroxide. Preferred transition metal salts include zinc chloride and zinc hydroxide. The most preferred transition metal salt is zinc chloride from a natural source such as is found in mines.

DETAILED DESCRIPTION OF THE PREFERRED EMBODIMENT

This disclosure provides pesticidal compounds and compositions that include oil extract from plants from the *Labiatae* and/or the *Verbenaceae* family. In particular, the pesticidal compounds can be formulated by combining organic phenolic compounds obtained from plant oil extracts with a transition metal salt. More particularly, the pesticidal compounds can be formulated by combining carvacrol and/or thymol obtained from plant oil extracts, with a transition metal salt.

I. Pests and Effects on Pests

Compounds and compositions of the invention generally have a detrimental effect on a pest in a desired or predetermined area. To have a detrimental effect on a pest in a desired or predetermined area can include any of the following. Pests that can be killed, have their growth inhibited, or repelled with pesticidal compounds and compositions of the invention include: insects, mites, eggs of insects or mites; fungus; microorganisms, including but not limited to bacteria, viruses, and parasites. An insect is an animal of class Insecta (or Hexapoda) of subphylum Uniramia of phylum Arthropoda, including but not limited to ants, flies, crickets, grasshoppers, butterflies, moths, spiders, ticks, and weevils. A mite is an arachnid of the family Acari or Acarina. A fungus is a member of the Kingdom fungi, so classified because they absorb food in solution directly through their cell walls and reproduce through spores. A microorganism is a living organism too small to be seen with the naked eye, including but not limited to bacteria, fungi, protozoans, and microscopic algae, and viruses.

The pesticidal compounds can be suitable for use as an insecticide, miticide, ovicide, fungicide, biocide, or a repellent. An insecticide is a chemical that kills or inhibits the growth of insects and other arthropods. A miticide is a chemical that kills or inhibits the growth of mites that feed on plants. An ovicide is a chemical that kills or inhibits the growth of eggs of insects or mites. A fungicide is a chemical that kills or inhibits the growth of fungi; including blights, mildews, molds, and rusts. A biocide is a chemical that kills or inhibits the growth of microorganisms. A repellent is a chemical that repels pests, including insects.

The growth of a pest has been inhibited if there has been a relative reduction in the number of pests in a desired or predetermined area. The growth of a pest has also been inhibited if the normal growth pattern of an individual pest has been modified so as to have a negative effect on the individual pest. The number of pests has been reduced by an action if there are less pests in a desired area than there would have been without the action. A pest has been repelled by an action if there are less pests present in a desired area than there would have been if the action had not been taken. An infestation of pests in a desired area is at least one pest in the desired area. An infestation has been prevented if there are less pests in the desired area after some action than there would have been without the action being taken. Prevention of an infestation by an action includes desired areas where there are no pests present but at least one pest would be present if not for the action taken.

Examples of desired or predetermined areas include but are not limited to, a plant, multiple plants, a crop of plants, an agricultural field, a houseplant, an animal (including humans, domestic animals, and non-domestic animals), a volume of space around an animal, and an area of land including the air above it.

II. Pesticidal Compound

A. Organic Phenolic Compound

The pesticidal compounds of the invention are made by reacting an organic phenolic compound such as carvacrol or thymol with a transition metal salt. Organic phenolic compounds as used in the invention can be made synthetically by known methods, or can be obtained from plant oil extracts.

Preferably, the organic phenolic compounds used in the invention are obtained from plant extracts. More preferably, the organic phenolic compounds used in the invention are obtained from plant extracts and are further separated to obtain carvacrol and thymol.

Figure 1:
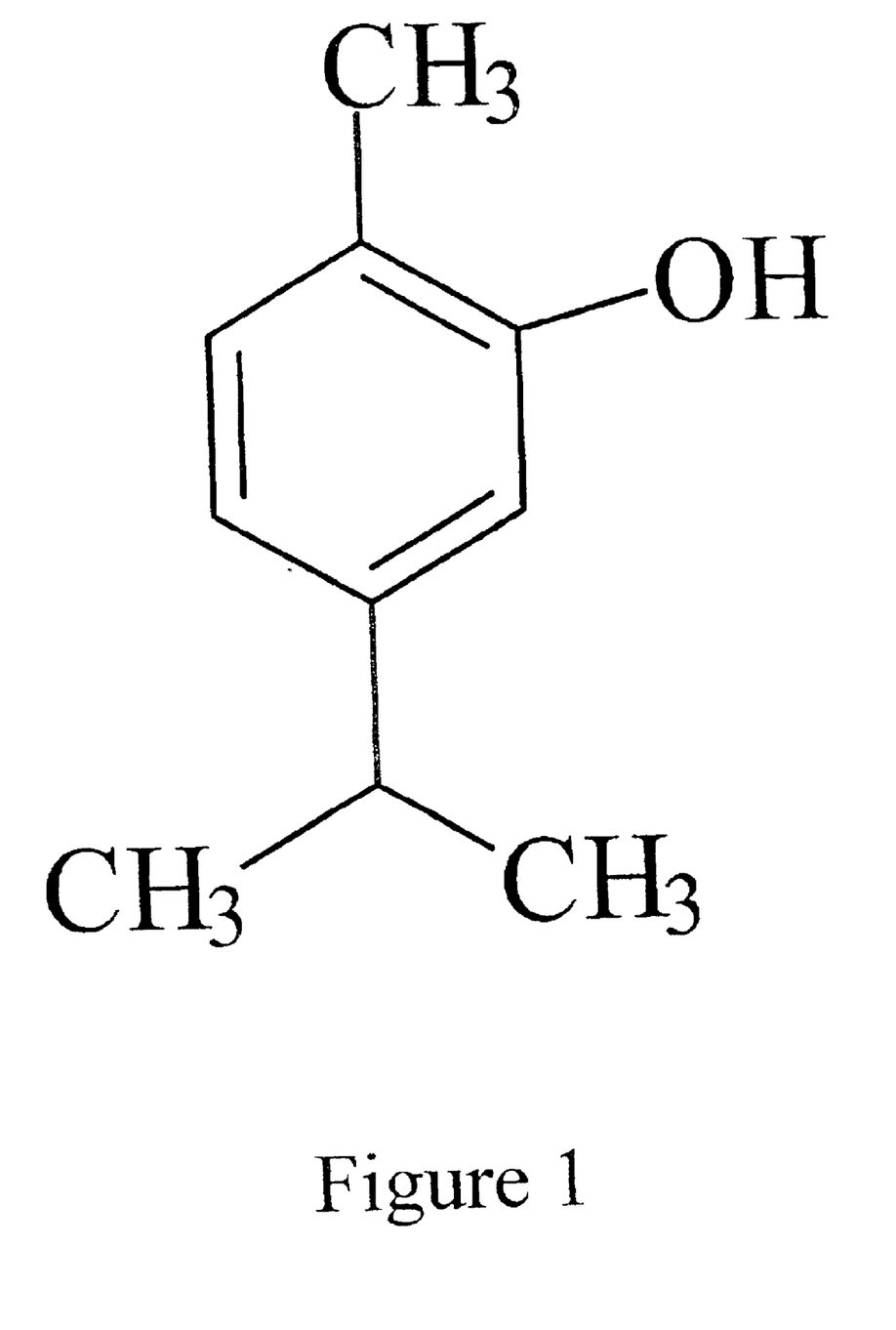
FIG. 1 shows a structural formula for carvacrol (also called 2-methyl-5-(1-methylethyl)phenol, isopropyl-o-cresol, 2-hydroxy-p-cymene, or isothymol).
Figure 2:
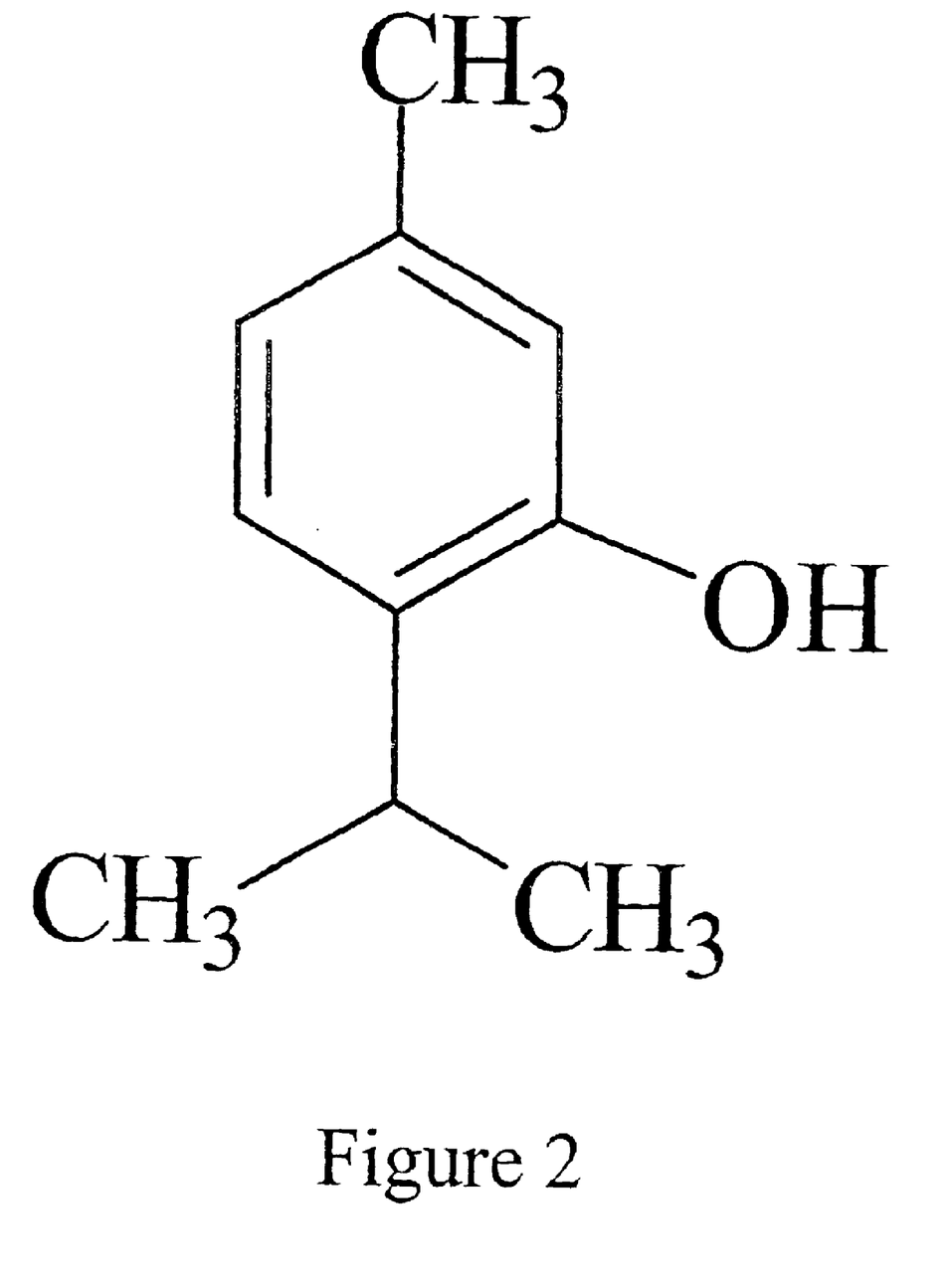
FIG. 2 shows a structural formula for thymol (also called 5-methyl-2-(1-methylethyl)phenol, 5-methyl-2-isopropyl-1-phenol, 1-methyl-3-hydroxy-4-isopropylbenzene, 3-p-cymenol, 3-hydroxy-p-cymene, or m-thymol).

Carvacrol, the structure of which is illustrated in FIG. 1, is a crystalline solid with a boiling point of about 233° C. at atmospheric pressure. Thymol, the structure of which is illustrated in FIG. 2, is a liquid that has a boiling point at atmospheric pressure of 237–238° C. Both compounds volatilize in water vapor.

1. Plants for Use in Extraction of Oils Containing Organic Phenols

In embodiments of the invention wherein the organic phenolic compounds are obtained from plant oil extracts, the oil is preferably extracted from a member of the *Labiatae* (also called *Lamiaceae*) or *Verbenaceae* family. Plants in the family *Labiatae* or *Verbenaceae* include hybrids of plants produced from individual plants in those two families.

The common name for members of the *Labiatae* family, a large family of mostly annual or perennial herbs, is the "mint family." The mint family is classified in the division Magnoliphyta, class Magnoliopsida, and order Lamiales. The *Labiatae* family includes about 200 genera, such as *Salvia, Rosmarinus, Mentha, Ocimum, Thymus, Marrubium, Monarda, Trichostema, Teucrium, Hyptis, Physostegia, Lamium, Stachys, Scutellaria* and *Lycopus*.

Plants which are preferably used for extraction of organic phenolic compounds include, but are not limited to, *Ocimum* spp., *Saturea* spp., *Monarda* spp, *Origanum* spp, *Thymus* spp., *Mentha* spp., *Nepeta* spp., *Teucrium gnaphalodes, Teucrium polium, Teucrim divaricatum, Teucrim kotschyanum, Micromeria myrifolia, Calamintha nepeta, Rosmarinus officinalis, Myrtus communis, Acinos suaveolens, Dictamnus albus, Micromeria fruticosa, Cunila origanoides, Mosla Japonoica Maxymowitz, Pycnanthemum nudum, Micromeria Juliana, Piper betel, Trachyspermum ammi, Lippia graveolens Escholcia splendens,* and *Cedrelopsis grevei,* as well as others.

In a preferred composition, the oil is extracted from *Esholtia splendens, Cedrelopsis grevei, Lippia graveolens* or a plant of the species *Nepeta,* including but not limited to *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinii, Nepeta nepetella, Nepeta sibthorpii, Nepeta subsessilis* and *Nepeta tuberosa.*

Most preferably, the oil is extracted from a hybrid plant produced from crossing *Nepeta racemosa, Esholtia splendens, Cedrelopsis grevei,* and *Lippia graveolens.*

2. Extraction of Carvacrol and Thymol from Plants a. Cultivating the Plant

Plants of the *Labiatae* and *Verbenacea* families are found throughout the world and are relatively easy to cultivate. To cultivate the plants, seeds, preferably those of plants that are expected to yield a high percentage (e.g., at least about 70 wt %, more preferably at least about 80 wt %), of organic phenolic compounds, are planted in fine loose soil, preferably in a sub-tropical climate. Hybrid seeds having a high percentage of organic phenolic compounds can be produced by known techniques. Crossing *Nepeta racemosa, Esholtia splendens, Cedrelopsis grevei,* and *Lippia graveolens* produces one such hybrid that is a preferred source of the organic phenolic compounds. The seeds are then cultivated using known agricultural techniques, such as watering, and artificial fertilizing. Most preferably, the plants are cultivated and grown without the use of any synthetic pesticides.

Because the leaves contain a high amount of oil upon blossoming, it is preferred that the plants be harvested soon after the plants begin to blossom. Preferably, the plants are harvested within 24 hours after blossoming, more preferably within 12 hours after blossoming. Most preferably, harvesting is undertaken early in the morning or late in the evening hours (after blossoming begins) when the leaves are not exposed to the sun.

Because the majority of the oil is found in the leaves and blossoms of the plant, it is preferred that only the leaves and blossoms be utilized in the extraction process. Use of other parts of the plant may increase impurities and decrease yield, but may be utilized.

b. Extracting Oil from the Plant

Oil containing organic phenolic compounds can be extracted from either dried or fresh plants, or a combination of both. If the plant is dried, the drying process is preferably undertaken in special drying houses that are constructed to allow for constant, free circulation of air. Preferably, the harvested leaves and blossoms are not exposed to direct sunlight, as exposure to sunlight may reduce the amount of active material present in the leaves.

To dry the product, the leaves and blossoms are arranged in 20–25 cm thick layers. To promote uniform drying, the layers should be turned up-side-down either manually or mechanically four times a day during the first three days of drying. Generally, the leaves are dried for about 7 to 8 days. After the leaves and blossoms are dried, the oil can be extracted by known methods, including distillation methods such as steam distillation.

Preferably, the oil is extracted in a two stage distillation process (double distillation). Preferably, the oil is first extracted by steam distillation (at a temperature of about 100° C.) to remove most impurities. Typically, after the first steam distillation, the extracted oil contains about 3% to about 4% by weight thymol; about 60% to about 70% carvacrol and about 26% to about 37% by weight impurities.

The steam-distilled oil is then distilled again at a temperature between about 180° C. to about 200° C. to remove additional impurities. Preferably, the redistilled oil is distilled yet again (a double re-distillation). If a double re-distillation process is used, the oil typically has a purity of greater than 90%, more preferably greater than 95%, and most preferably to 99%. Although yield tends to be lower when a double re-distillation process is used, typically about 1 to 10 kilograms, more typically about 3 to 7 kilograms of oil, are obtained for every 100 kilograms of dried leaves and blossoms.

In a steam distillation process, the distillation column generally has two output tubes: one for oil (at the base of the column) and one for water vapor (at the top of the column). A water source is positioned under the leaves and blossoms and is heated to about 100° C. preferably under a pressure of about 20 bar to about 25 bar (increased pressure will tend to reduce the distillation time). The steam passes through the leaves and blossoms, thereby creating oil droplets. Because the water vapor is lighter than the oil droplets, the water droplets flow out of the output tube positioned at the top of the distillation column and the oil droplets flow out of the output tube positioned at the base of the distillation column. The distillation process is carried out for about 1 to about 5 hours, more typically about 2 to about 3 hours.

3. Synthetic Production of Organic Phenolic Compound

Organic phenolic compounds used in the invention can alternatively be prepared by synthetic methods. Methods for synthetically producing organic phenolic compounds such as carvacrol and thymol are known. See for example *Organic Chemistry* by Morrison & Boyd, 2d ed. 1971 at page 815. Additionally, these compounds are available from chemical manufacturers and are listed in the Merck Index. Although the organic phenolic compounds may be synthetically produced, it is preferred that the compounds by extracted from plants. Because phenol is used to synthesize carvacrol and isopropyl-cresol, the resulting product tends to contain residual phenol (less than 1%). It is generally undesirable to administer a composition containing phenol to an animal because phenol can be highly mutagenic and carcinogenic.

B. Salts

The pesticidal compounds of the invention are made by reacting an organic phenolic compound such as carvacrol or thymol with a transition metal salt or alternatively with a salt containing a divalent cation. Preferably, the pesticidal compounds of the invention are made by reacting an organic phenolic compound with a transition metal salt.

1. Transition Metal Salt

The transition metals are the thirty-eight (38) elements in groups 3 through 12 of the periodic table. As with all metals, the transition elements are both ductile and malleable, and conduct electricity and heat. The transition metals are defined by their valence electrons, or the electrons that are used to combine with other elements. The transition metals have valence electrons that are present in more than one shell. Because of this valence electron configuration, they are able to exhibit a number of different oxidation states.

The transition metals include the following elements: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium seaborgium, bohrium, hassium, meitnerium, ununnilum, unununium, unubium. Preferred transition metals for use in making compounds of the invention are those that commonly exhibit an oxidation state of +2, examples of these transition metals are: nickel, copper, zinc, and cadmium. The most preferred transition metals for use in the invention are zinc, nickel or copper.

The transition metal can, but need not, be utilized in combination with an anion. An anion is any negatively charged element. Preferably, the transition metal is combined with chloride, fluoride, hydride, hydroxide, nitrate, oxide, or sulfide. More preferably, the transition metal is combined with chloride, oxide, or sulfate. Most preferably, the transition metal used is zinc chloride ($ZnCl_2$), zinc sulfate ($ZnSO_4$), or a transition metal salt that is a natural or a synthetic natural compound. As used herein, the term "natural" refers to a substance or mixture that occurs in nature that is not chemically synthesized. "Synthetic natural compound" refers to compounds that are synthesized but whose counterpart can be found in nature. An example of a natural compound is sodium chloride obtained from the ocean. An example of a synthetic natural compound is sodium chloride that has been synthesized.

2. Divalent Cation Containing Salt

Salts containing divalent cations (other than transition metal ions), i.e. cations with a +2 charge, can also be reacted with the organic phenolic compound to make the pesticidal compounds of the invention. Examples of such +2 cations that can be the cation of salts useful in the invention include benzllium, calcium, magnesium, strontium, barium, or radium. Preferred +2 cations include calcium and magnesium. More preferably, the +2 cation, if not a transition metal, is magnesium. The salt can contain any anion, examples of which include, hydroxide, chloride, nitrate, sulfate, phosphate, carbonate, borate, and fluoride. Preferably, the divalent cation containing salt is a natural or a synthetic natural compound. The terms "natural" and "synthetic natural compound" have the meanings given them above.

C. Formation of Pesticidal Compound

1. Reaction of Organic Phenolic Compound with A Salt

Pesticidal compounds of the invention are formed by reacting an organic phenolic compound with a salt.

In one embodiment of the invention, the reaction of the organic phenolic compound with the salt is carried out in the following manner. The organic phenolic compound is combined with the salt. The mixture is then mixed at high speed (e.g. 1000 revolutions/minute) for a specified time (e.g. 30 minutes). The ratio of the weight of the organic phenolic compound to the weight of the salt in the reaction is preferably 50:50 to 75:25, respectively. More preferably, the ratio of the weight of the organic phenolic compound to the weight of the salt is 55:45 to 70:30. Most preferably, the ratio of the weight of the organic phenolic compound to the weight of the salt is from 60:40 to 65:35.

Figure 3:
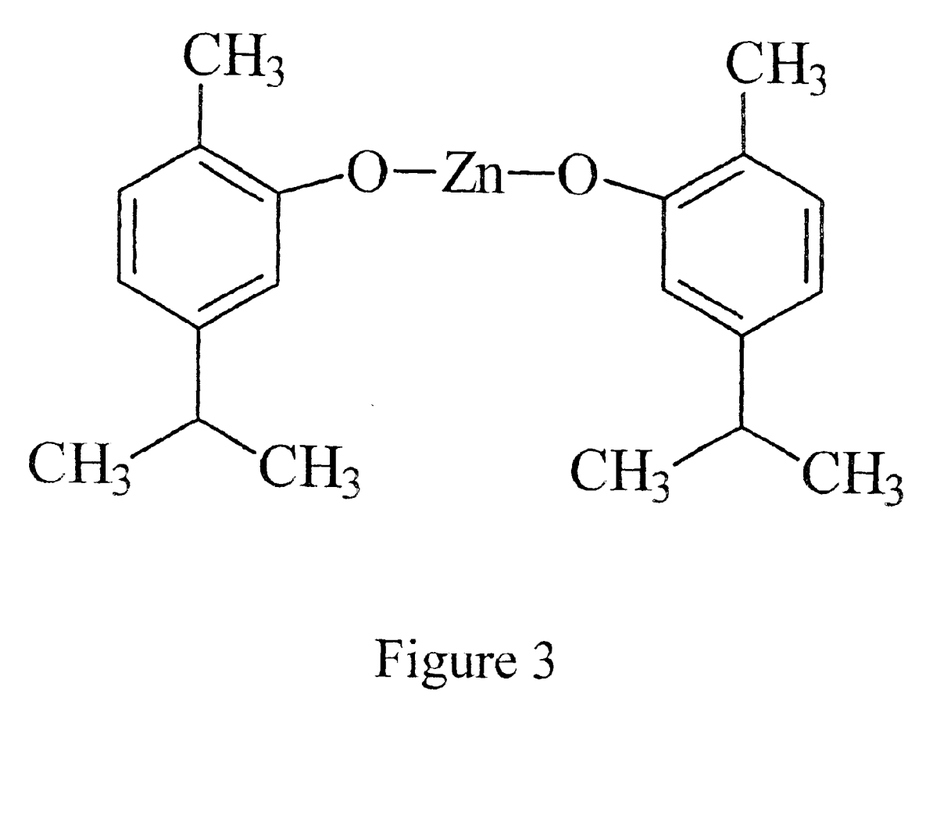
FIG. 3 shows a structural formula of carvacrol reacted with zinc chloride.
Figure 4:
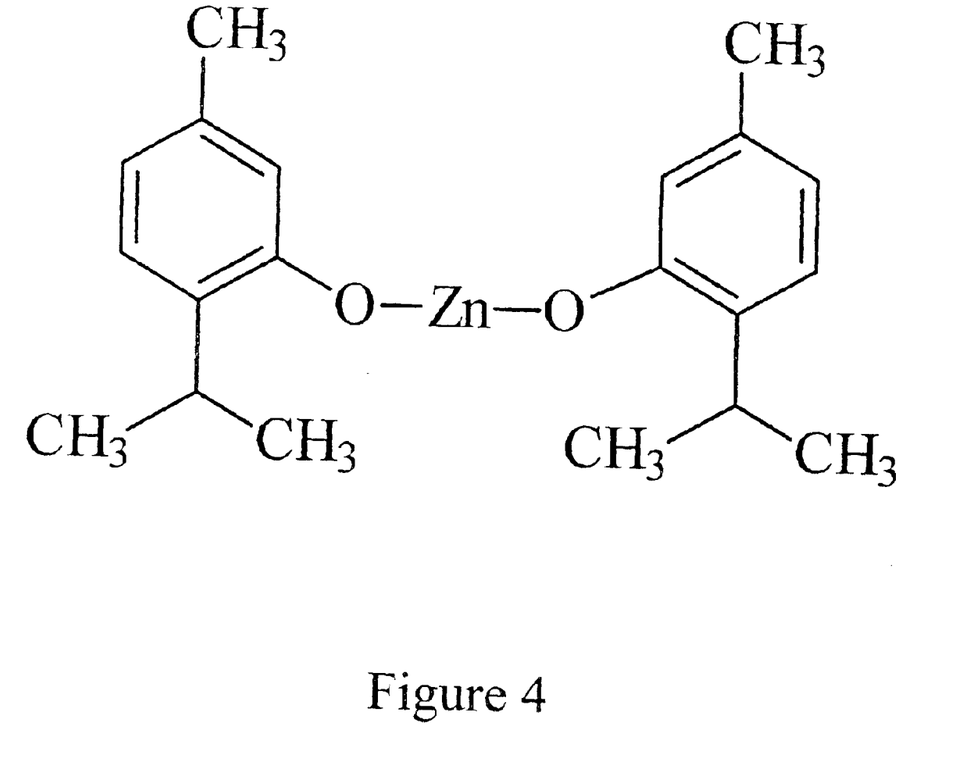
FIG. 4 shows a structural formula of thymol reacted with zinc chloride.

The possible product of the reaction of an organic phenolic compound with a salt is exemplified by FIGS. 3 and 4, which illustrates the products of the reaction of carvacrol and thymol respectively with zinc chloride. It is thought, but not relied upon that the salt forms a complex with the ionized organic phenolic compound. The pesticidal compounds are named based on the organic phenolic compound from which they were produced. Therefore, a pesticidal compound produced by reaction of carvacrol with a salt would be called a carvacrol pesticidal compound. Similarly, a pesticidal compound produced by reaction of thymol with a salt would be called a thymol pesticidal compound. More specifically, the pesticidal compounds can be referred to by designating the cation associated with the organic phenolic compounds. Therefore, a pesticidal compound produced by reaction of carvacrol with zinc chloride would be called zinc carvacrolate.

Specific reactions of organic phenolic compounds with salts are further illustrated in examples 3 and 4 of the working examples.

2. Mixture of Formed Pesticidal Compounds

The pesticidal compounds of the invention can be used singly, or in combination. Preferably, the pesticidal compounds are used as a mixture of at least two pesticidal compounds. More preferably, the pesticidal compounds are used as a mixture of a carvacrol pesticidal compound and a thymol pesticidal compound. Most preferably, the pesticidal compounds are used as a mixture of zinc carvacrolate and zinc thymolate.

If a carvacrol pesticidal compound and a thymol pesticidal compound are mixed together, the ratio of carvacrol pesticidal compound to thymol pesticidal compound can range from 100:1 to 1:1 respectively. Preferably, the ratio of carvacrol pesticidal compound to thymol pesticidal compound is from 50:1 to 5:1 respectively. More preferably the ratio of carvacrol pesticidal compound to thymol pesticidal compound is 10:1 respectively.

One specific example of the mixture of pesticidal compounds is illustrated in example 5 of the working examples.

D. Mode of Action of Pesticidal Compounds

1. Mode of Action of Pesticidal Compound as an Insecticide or Miticide

It is believed but not relied upon that the pesticidal compounds of the invention have at least two different modes of action. The pesticidal compounds may act in the same manner as oil insecticides in that they suffocate all developmental stages of the insect; egg, immature form, or adult form. Insecticides that function in this way are beneficial because they are not toxic to the neurological system of animals and have very little negative effects on the applicator. Alternately, the pesticidal compound may act on an inhibitory mechanism called the GABA (gamma-aminobutyric acid) receptor. This receptor operates by increasing the permeability of neurons to chloride ions. When chloride ions are prevented from entering the neurons, the "calming" effects of GABA are increased.

2. Mode of Action of Pesticidal Compound as a Fungicide or a Biocide

When used as a fungicide or a biocide, the pesticidal compounds of the invention are thought to have a single mode of action. It is believed but not relied upon that the mode of action is similar to the activity of benzyl alcohol, phenol and polyphenols in that the pesticidal compounds destroy the cell membrane of the microorganism, causing cell death. The pesticidal compounds are capable of dissolving lipids. The membranes of fungus, bacteria, and parasites have lipids as a component. When the pesticidal compounds come into contact with the pests' membranes, the lipids within the membranes will be dissolved. This will cause destruction of the membrane, and eventually death of the pests' cells because of the destruction of the membrane. The British Pharmacopoeia, Edition 1996, reports that microorganisms do not build resistance to benzyl alcohol, phenols, polyphenols, and similar products, therefore, based on this mode of action, there should not be any resistance built up to the pesticidal compounds of the invention for use as a fungicide or biocide.

3. Mode of Action of Pesticidal Compound as a Repellent

The pesticidal compounds of the invention can also be used as repellents for insects specifically. It is believed but not relied upon that the repellent properties of the pesticidal compounds of the invention result from the pungent odor that is associated with the organic phenolic compounds that are the precursors of the pesticidal compounds.

E. Effect on Environment

Because the pesticidal compounds are based on organic phenolic compounds, they are readily degraded in the environment. They are therefore particularly well suited for treatment of foodstuff crops because they can be used without concern of environmental build up. The group of natural phenols, of which carvacrol and thymol are members, are generally readily degradable in the environment. This results in little or no accumulation in the environment, or in living organisms. Aerobic bacterial degradation involves complete breakdown to carbon dioxide. Anaerobic degradation results in Benzyl Co-A derivatives. Natural phenols can also be condensed to humic acids in soils. Preferred pesticidal compounds of the invention also contain zinc. Although zinc is not readily degraded in the environment, it is taken up by several varieties of plants.

Additionally, the pesticidal compounds do not appear to be mutagenic or carcinogenic.

III. Pesticidal Composition

The pesticidal compounds of the present invention, produced as discussed above are formulated into pesticidal compositions as discussed below.

A. Formulation of Pesticidal Compositions

Pesticidal compositions of the invention comprise mixtures or solutions containing at least one pesticidal compound of the present invention. The pesticidal compounds of the invention can be used alone or in combination. Preferably the pesticidal compounds of the present invention are used as a combination of at least one carvacrol pesticidal compound and at least one thymol pesticidal compound.

Pesticidal compositions of the invention may also contain carriers or diluents. A carrier or diluent is an inert material used in making different formulations of pesticidal compounds. The specific carrier used in any pesticidal composition depends on the pest it is meant to eradicate, how the pesticidal composition will be applied (whether in a spray or dust form for example) and where the pesticidal composition will be applied.

Formulation of the pesticidal compound into the pesticidal composition is an important aspect of pesticide manufacturing because of the need to make a pesticidal composition that will both work as intended and will comply with Federal and State regulations. The producers of the pesticidal compound can formulate the compound themselves or can have the pesticidal compound formulated by a secondary entity.

There are a number of different general classes of pesticide formulations, including for example sprays, dusts, granules, and aerosols.

1. Spray Formulations

Spray formulations include aqueous solutions, water-soluble powders, emulsifiable concentrates, water miscible liquids/powders (for pesticidal compounds that are soluble in water), wettable powders or water-dispersible powders, flowable/sprayable suspensions or suspension concentrates, and oil solutions. Although sprays are a very popular method of applying pesticides, only a small number of pesticides are sufficiently soluble in water to be formulated into an aqueous solution, water-soluble powder, or water miscible liquid or powder. Therefore, most spray formulations need an organic solvent or a specialized formulation to enable them to be mixed with water for spray application.

An important spray formulation for the invention is an emulsifiable concentrate. In an emulsifiable concentrate, a concentrated organic solvent based solution of the pesticidal compound (or the pesticidal compound alone if it is a liquid at room temperature) is added to an emulsifier. An emulsifier is a detergent-like (surfactant) material that allows microscopically small oil droplets to be suspended in water to form an emulsion. The concentrate is thereby dispersed evenly throughout an aqueous solution and generally remains suspended for an extended period of time (days).

Emulsifiers useful in the invention include Tween 200, Tween 600, sorbitol (polysorbate 80), propylene glycol, polyethylene glycol, ethanol (ethyl alcohol) and methanol (methyl alcohol). Another type of surfactant that can be used as an emulsifier for pesticide formulations is the phosphate esters. Examples of commercially available phosphate ester surfactants include: butyl phosphate, hexyl phosphate, 2-ethylhexyl phosphate, octyl phosphate, decyl phosphate, octyldecyl phosphate, mixed alkyl phosphate, hexyl polyphosphate, and octyl polyphosphate. Preferably, the emulsifier used is either Tween 200, sorbitol 80, propylene glycol, polyethylene glycol, or ethyl alcohol. More preferably, sorbitol 80 is used as the emulsifier if an emulsifiable concentrate of a compound of the invention is to be formulated.

Emulsifiable concentrates are the preferred spray formulation for the pesticidal compounds of the invention because of the low solubility of the pesticidal compounds in water, and their ability to maintain a constant pesticidal compound concentration throughout spraying.

Wettable powders or water-dispersible powders are also an important spray formulation. Wettable powders are made by mixing the pesticidal compound with a fine dust (generally clay or talc) and a wetting agent (a dry soap or detergent). This mixture is then dispersed in water before spraying. The wetting agent will act as an emulsifier in the aqueous solution and cause the otherwise insoluble pesticidal compound to dissolve in water. Emulsifiable concentrates are preferred over wettable powders for most applications because the wettable powder aqueous solution will tend to "settle" quickly while requiring agitation in order to keep a constant concentration of pesticidal compound while spraying.

Flowable/sprayable suspensions or suspension concentrates are another method of creating a spray formulation with a pesticidal compound that is insoluble in water. A flowable/sprayable suspension is a suspension of very finely ground dust diluent and pesticidal compound in a non-solvent liquid (generally water). The suspension will then mix well with water and can be sprayed. Flowable/sprayable suspensions suffer the same disadvantage as wettable powders because they tend to "settle" out and give varying concentrations of pesticidal compound throughout spraying.

An oil solution is another method of creating a spray formulation with a pesticidal compound that is insoluble in water. The pesticidal compound is dispersed in oil and applied as an oil based spray. This formulation is convenient for ready-to-use pesticides where further handling by the user is not desired.

The concentration of pesticidal compounds in spray formulations ranges from 0.1% to 15% by weight. Preferably, the concentration of pesticidal compounds in spray formulations ranges from 0.5 to 10% by weight. More preferably, the concentration of pesticidal compounds in spray formulations ranges from 0.75% to 7.5% by weight.

2. Dust Formulations

In a dust formulation, the pesticidal compound is mixed with a solid particulate diluent (preferably one with a size range of 50–100 $\mu$m). The dust formulation is then mixed with the air through the aid of a dusting machine. Although dust formulations have historically been the easiest to make and apply, application rates, and pesticidal compound concentrations have to be exceedingly high. Further, even though the amount of pesticidal compound applied is very high, the actual amount of the pesticidal compound that reaches the target is generally low because the dusts are prone to drift.

Dust formulations can be utilized in formulations of the pesticidal compounds of the present invention. Preferred diluents for use in dust formulations are silicon dioxide, zinc oxide, talc, diatomaceous earth, clays, calcium carbonate, wheat flour, and powdered nut hulls.

The concentration of pesticidal compounds in dust formulations ranges from 0.10 to 20% by weight. Preferred concentrations of pesticidal compounds in dust formulations ranges from 5 to 15% by weight. More preferably, the concentrations of pesticidal compounds in dust formulations ranges from 7 to 12% by weight.

3. Granular Formulations

The pesticidal compounds of the invention can also be formulated into granular formulations. Granules are small pellets (usually 0.3–1.3 mm) of inert carrier (usually clay) mixed with the pesticidal compound to give the desired concentration. Granules can be formulated to allow a rapid release, or an extended release of the pesticidal compound over time. Granular formulations are useful for relatively small scale (garden or houseplant) applications, and in applications where safer handling is desired.

The concentration of pesticidal compounds in granular formulations ranges from 0.1 to 20% by weight. Preferred concentrations range from 5 to 15% by weight. More preferably, the concentration of pesticidal compounds in dust formulations ranges from 7 to 12% by weight.

4. Aerosol Formulation

The pesticidal compounds of the invention can also be formulated into aerosol formulations. In order to use an aerosol formulation, the pesticidal compound must be soluble in a pressurized, volatile, petroleum solvent. Upon application of the aerosol formulation, the solvent evaporates leaving micro-droplets of the pesticidal compound suspended in the air. Aerosol formulations are useful for indoor applications, or small scale outdoor applications.

The concentration of pesticidal compounds in aerosol formulations ranges from 0.1% to 15% by weight. Preferably, the concentration of pesticidal compounds in aerosol formulations ranges from 0.5 to 10% by weight. More preferably, the concentration of pesticidal compounds in aerosol formulations ranges from 0.75% to 7.5% by weight.

5. Further Preparation of Pesticidal Composition

The formulated pesticidal composition can either be applied directly or can be diluted further before application. The diluent depends on the specific treatment to be accomplished, and the method of application. For example, a pesticidal composition that is to be applied to trees could be diluted further with water to make it easier and more efficient to spray with known spraying techniques. Preferably, the formulated pesticidal composition is diluted from 1:100 to 1:10 with water. More preferably, the pesticidal composition is diluted 1:10 with water.

B. Illustrative Pesticidal Compositions Containing Pesticidal Compound

Pesticidal compositions of the invention are exemplified by the formulations given below.

| | |
|---|---|
| Spray formulation for use as fungicide: | |
| Pesticidal Compound or Compounds | 3.5% |
| Carriers | 96.5% |
| Spray formulation for use as a biocide: | |
| Pesticidal Compound or Compounds | 5% |
| Carriers | 95% |
| Spray formulation for use as an insecticide: | |
| Pesticidal Compound or Compounds | 7.5% |
| Carriers | 92.5% |
| Dust formulation for use as a fungicide: | |
| Pesticidal Compound or Compounds | 4% |
| Carriers | 96% |
| Dust formulation for use as a biocide: | |
| Pesticidal Compound or Compounds | 7.5% |
| Carriers | 92.5% |
| Dust formulation for use as an insecticide: | |
| Pesticidal Compound or Compounds | 10% |
| Carriers | 90% |

In the above formulations, the pesticidal compound preferably used is the 10:1 mix of zinc carvacrolate and zinc thymolate. The carrier for the spray formulation is preferably either sorbitol or an equal mix of propylene glycol, polyethylene glycol, and ethyl alcohol.

C. Application of the Pesticidal Compositions

Pesticidal compositions, either diluted or undiluted, can be applied in a number of different ways. For small scale application of a liquid pesticidal composition, backpack tanks, hand-held wands, spray bottles, or aerosol cans can be utilized. For somewhat larger scale application of liquid pesticidal compositions, tractor drawn rigs with booms, tractor drawn mist blowers, airplanes or helicopters equipped for spraying, or fogging sprayers can all be utilized. Small scale application of solid formulations can be accomplished in a number of different ways, examples of which are: shaking product directly from the container or gravity-application by human powered fertilizer spreader. Large scale application of solid formulations can be accomplished by gravity fed tractor drawn applicators, or similar devices.

IV. WORKING EXAMPLES

Example 1

Production of Hybrid Plant

A hybrid plant is produced by crossing the following species of plants belonging to the *Labiatea* and *Verbenaceae* families: *Nepeta racemosa, Esholtia splendens, Cedrelopsis grevei,* and *Lippia graveolens.* The hybrid plant is produced with methods well known in the art to give a resulting hybrid plant with the following proportions of the plants: 20% *Nepeta racemosa:* 30% *Esholtia splendens:* 20% *Cedrelopsis grevei:* 30% *Lippia graveolens.*

Example 2

Extraction of Carvacrol and Thymol from *Nepeta cataria*

Carvacrol and thymol were extracted from *Nepeta cataria* using a two stage distillation process. In the first stage, dried leaves were extracted using a steam distillation process. After the distillation, the oil was cooled to room temperature for at least 72 hours.

The oil from the steam distillation process was then re-distilled in a second stage distillation process. In the re-distillation, the oil was heated to a temperature of about 186° C. for about 1 hour to remove remaining impurities such as linalool, barneol, pimen, and cimen. Generally, the impurities have a boiling point of about 150° C. In contrast, both carvacrol and thymol have a boiling point of about 230° C. to 240° C. Thus, a temperature of 180° C. will typically not remove or damage the organic phenolic products.

The oil was again allowed to cool for at least 72 hours. This step is thought to stabilize the oil.

After the oil is cooled, the redistillation is repeated at a temperature of 180° C. for 30 minutes to eliminate almost all of the remaining impurities. The double re-distillation process produced an oil having a purity between 95% and 98%.

After the second re-distillation, the oil was allowed to cool for at least 72 hours before further processing was undertaken on it.

Example 3

Separation of Carvacrol from Thymol

Carvacrol and thymol were separated by incubating the distilled oil at a temperature of −25° C. for about 6 hours. Carvacrol remains as a liquid and thymol is precipitated out as crystals. The two compounds were then separated via filtration.

Example 4

Preparation of Carvacrol Pesticidal Compound

The carvacrol pesticidal compound was formed by reaction of carvacrol with zinc chloride. 65 wt-% of carvacrol, prepared as above, was combined with 35 wt-% of zinc chloride. The combination was mixed at 1000 RPM for about 30 minutes in the high speed mixer discussed above.

Example 5
Preparation of Thymol Pesticidal Compound

The thymol pesticidal compound was formed by reaction of thymol with zinc chloride. 60 wt-% of thymol, prepared as above, was combined with 40 wt-% zinc chloride. The combination was mixed at 1000 RPM for about 30 minutes in the high speed mixer discussed above.

Example 6
Combination of Carvacrol and Thymol Pesticidal Compound

The carvacrol pesticidal compound, prepared as above, was mixed with the thymol pesticidal compound prepared as above. The two were mixed in a weight ratio of carvacrol pesticidal compound to thymol pesticidal compound of 10:1. The mixing of the two pesticidal compounds is accomplished at 500 RPM for about 3 minutes in the high speed mixer discussed above.

Example 7
Use of Pesticidal Composition as Fungicide

An experiment was conducted on a rose plant that had been infected by fungus, specifically *Clasterosprium carpophilum*. The fungus had colonized the leaves of the plant, causing holes in the leaves. The leaves of the rose had begun to drop. If left untreated, the rose would cease to flower and eventually die.

The fungicidal composition utilized herein was a water soluble formulation at a concentration of 3.5 wt % of a mixture (10:1) of carvacrol pesticidal compound and thymol pesticidal compound. Sorbitol at 96.5 wt-% was used as the carrier. The 3.5% solution was then diluted 1:10 with water. The resulting fungicidal composition was applied with a hand sprayer.

Forty-eight (48) hours after the first (and only) treatment, the fungus was no longer visually present on the leaves of the rose.

Example 8
Use of Pesticidal Composition as a Fungicide

An experiment was conducted on soybean plants, *Glycine max*. The soybean plants were afflicted with a fungus, *Leptosphaerulina trifolli*. The fungus attacks the leaves of the plants and if left untreated would eventually cause plant to die.

The fungicidal composition utilized herein was a water soluble formulation at a concentration of 3.5 wt-% of a mixture (10:1) of carvacrol pesticidal compound and thymol pesticidal compound. Sorbitol at 96.5 wt-% was used as the carrier. The 3.5% solution was then diluted 1:100 with water. The resulting fungicidal composition was applied with a hand sprayer.

After one treatment, the fungal infection was no longer readily apparent on the plant.

Example 9
Use of Pesticidal Composition as a Biocide

An experiment was conducted on seven (7) cherry trees. The cherry trees were infected by bacteria, *Agrobacterium radiobacter*. The bacteria is thought to attack the space between the cells of the tree, thereby damaging the metabolism of the tree. The bacteria generally halts growth of the trees, with younger trees being more susceptible. The cherry trees utilized in the experiment were infected with *Agrobacterium radiobacter*, and had not grown appreciably in the two months they had been planted.

The biocidal composition utilized herein was a water soluble formulation at a concentration of 5 wt-% of a mixture (10:1) of carvacrol pesticidal compound and thymol pesticidal compound. Sorbitol at 95 wt-% was used as the carrier. The 5% solution was then diluted 1:10 with water. The biocidal composition was applied with a hand sprayer. The trees were sprayed early in the morning once a week for six (6) weeks.

After six weeks of treatment, the cherry trees began to grow, evidencing that the bacteria infection had been eradicated. Because *Agrobacterium radiobacter* generally attacks younger trees, a preventive course of action would be to spray as yet non-infected trees once a week for one to two months.

Example 10
Use of Pesticidal Composition as a Pesticide for Plant Treatment An experiment was conducted on twelve (12) apple trees. The goal of the experiment was to prevent infiltration of a parasite, *Carpocapsa pomonella*. *Carpocapsa pomonella* causes the fruit to drop from the tree prematurely, and the fruit itself to have parasites in it. *Carpocapsa pomonella* infects other fruit and nut trees as well.

The insecticidal composition used herein was a water soluble formulation at a concentration of 7.5 wt-% of a mixture (10:1) of carvacrol pesticidal compound and thymol pesticidal compound. Sorbitol at 92.5 wt-% was used as the carrier. The 7.5% solution was then diluted 1:10 with water. The insecticidal composition was applied with large scale agricultural sprayers to the leaves, developing fruit and bark of the trees. The treatment was begun immediately prior to development of the apples, and was repeated once a day for 15 days.

The treated apple trees were not infiltrated by *Carpocapsa pomonella*.

Example 11
Use of Pesticidal Composition as an Insecticide for Plant Treatment An experiment was conducted in a vineyard known to have the insect *Otiorrhynchus ligustici* present. *Otiorrhynchus ligustici* will eat the leaves of the grapes, especially the newly formed leaves. Destruction of the leaves will hinder growth of the vine and will likely prevent grape formation. *Otiorrhynchus ligustici* has become resistant to the insecticides that are commonly used in vineyards so they pose a significant threat to the vineyard.

The insecticidal composition used herein was a water soluble formulation at a concentration of 7.5 wt-% of a mixture (10:1) of carvacrol pesticidal compound and thymol pesticidal compound. Sorbitol at 92.5 wt-% was used as the carrier. The 7.5 wt-% solution was then diluted 1:10 with water. The insecticidal composition was applied with large scale agricultural sprayers to the leaves, and fruit of the vines. The insecticidal composition was applied once every ten (10) days for two months.

The *Otiorrhynchus ligustici* began to die one to two hours after the first treatment with the insecticidal composition, and 24 hours after the treatment, no live insects were observed. After two (2) months of treatment with the insecticidal composition, *Otiorrhynchus ligustici* ceased to be a problem for the vineyard.

Example 12
Use of Pesticidal Composition as Insecticide for Home Use

An experiment was conducted to determine the efficacy of the pesticidal composition for the destruction of common household insects.

The insecticidal composition used herein was a water soluble formulation at a concentration of 5 wt-% of a mixture (10:1) of carvacrol pesticidal compound and thymol pesticidal compound. Sorbitol at 95 wt-% was used as the carrier. The 5% solution was then diluted 1:10 with water. The resulting solution was then put in a spray bottle under pressure. The product was sprayed directly onto the insects. The amount applied was dependent on the particular insect. The following table shows the amount applied and the time necessary to kill the insect.

| Insect | Amount Applied (ml) | Time Until Death (secs) |
|---|---|---|
| Houseflies | 0.3 | 60 |
| Mosquitoes | 0.1 | 30 |
| Ants | 0.1 | 180 |
| Fruit Flies | 0.2 | 20 |
| Moths (10) | 0.1 | 5 |
| Ticks | 0.3 | 10 |
| Termites (7) | 0.5 | 15 |

Example 13

Use of Pesticidal Composition as Insecticide for Human Use

An experiment was conducted to determine the efficacy of the pesticidal composition for the destruction of hair lice on a child.

The insecticidal composition used herein was a water soluble formulation at a concentration of 5 wt-% of a mixture (10:1) of carvacrol pesticidal compound and thymol pesticidal compound. Sorbitol at 95 wt-% was used as the carrier. The 5% solution was mixed with an off the shelf shampoo. The afflicted child's hair was lathered with 5–10 ml of the shampoo, and the shampoo was kept on the hair for 30 minutes at which time it was rinsed out normally. The shampooing was repeated in 48 hours, and again at seven days after the original treatment.

The lice were observed to be dead immediately after the first treatment. The treatment after 7 days was done to allow any eggs present in the hair to hatch before a final treatment. After the three treatment course, there were no lice or eggs present in the previously afflicted child.

Example 14

Use of Pesticidal Composition as Insecticide for Treatment of Dogs

An experiment was conducted to determine the efficacy of the pesticidal composition for destruction of ticks. Two (2) dogs with observed tick infestation were treated.

The insecticidal composition used herein was a powder formulation at a concentration of 10 wt-% of a mixture (10:1) of carvacrol pesticidal compound and thymol pesticidal compound. The powder was spread on the entire body of the dog making sure to protect the eyes from exposure. The dogs were treated once a day for three (3) days.

No ticks were observed on either of the dogs after the first treatment.

Example 15

Use of Pesticidal Composition as an Insect Repellant

An experiment was conducted to determine the efficacy of the pesticidal composition as an insect repellent for use on humans. Three (3) humans embarking on an outdoor expedition (fishing) were involved in this experiment.

The insecticidal composition utilized herein was a water soluble formulation at a concentration of 5 wt-% of a mixture (10:1) of carvacrol pesticidal compound and thymol pesticidal compound. Sorbitol at 95 wt-% was used as the carrier. The 5% insecticidal composition was further formulated into an ointment. The ointment was formulated with olive oil, petroleum jelly, gel cellulose and water. The ointment containing the 5% insecticidal composition was applied to all exposed skin areas: face, hands and legs before beginning fishing.

After 8 hours of exposure to mosquitoes, flies, etc. there was not any observation of mosquito bites on the subjects. A similar experiment was conducted with individuals spending time in the woods and again no mosquito bites were observed.

Example 16

Use of Pesticidal Composition as Pesticide Treatment of Parasites

An experiment was conducted to determine the efficacy of the pesticidal composition as a treatment for the parasite, *Demodex canis* in dogs. The parasite causes large, significant, and deep damage to the skin. The parasite infects the hair follicles and is therefore very difficult to treat effectively. Five (5) dogs, 3 male and 2 female, infected with the parasite, who were non-responsive to other anti-parasitic products were treated.

The pesticidal composition used herein was a water soluble formulation at a concentration of 12 wt-% (10:1) of carvacrol pesticidal compound and thymol pesticidal compound. The carrier was a combination of petroleum jelly, olive oil, and polyethylene glycol. The infected skin of the dog was treated twice a day for seven days. Approximately 1 ml of the ointment per 2 $cm^2$ of skin was applied. The ointment was applied to the infected area and rubbed so that it was absorbed in the skin.

Small improvements were seen in the affected areas after 72 hours. A substantial improvement was seen after seven (7) days of treatment.

We claim:

1. A pesticidal composition comprising:

(a) carvacrol (b) thymol; and (b) at least one salt comprising a transition metal.

2. The pesticidal composition of claim 1, wherein the thymol and carvacrol are extracted from a member of the family *Labiatae* or *Verbenacea*.

3. The pesticidal composition of claim 2, wherein the thymol and carvacrol are extracted from a plant formed from genetically crossing *Nepeta racemosa, Escholcia splendens, Cedrelopsis grevei,* and *Lippia graveolens*.

4. The pesticidal composition of claim 1, wherein the transition metal comprises nickel, copper, zinc, cadmium, or combinations thereof.

5. The pesticidal composition of claim 4, wherein the transition metal salt comprises zinc.

6. The pesticidal composition of claim 4, wherein the transition metal salt further comprises chloride, sulfate, oxide, hydroxide, hydride, or combinations thereof.

7. The pesticidal composition of 6, wherein the transition metal salt comprises zinc chloride, zinc sulfate, or combinations thereof.

8. The pesticidal composition of claim 1, additionally comprising a carrier.

9. The pesticidal composition of claim 1, wherein the pesticidal compound is used as an insecticide, miticide, ovicide, fungicide, biocide, insect repellant, or combination thereof.

10. A pesticidal composition comprising:
(a) carvacrol
(b) thymol;
(c) at least one transition metal salt; and
(d) at least one carrier.

11. The pesticidal composition of claim 10, wherein the ratio of the weight of carvacrol to the weight of thymol is about 100:1 to about 1:1.

12. The pesticidal composition of claim 11, wherein the ratio of the weight of carvacrol to the weight of thymol is about 50:1 to about 5:1.

13. The pesticidal composition of claim 12, wherein the ratio of the weight of carvacrol to the weight of thymol is about 10:1.

14. The pesticidal composition of claim 10, wherein the thymol and carvacrol are extracted from a member of the family *Labiatae* or *Verbenacea*.

15. The pesticidal composition of claim 14, wherein the thymol and carvacrol are extracted from a plant formed from crossing *Nepeta racemosa, Escholcia splendens, Cedrelopsis greve,* and *Lippia graveolens.*

16. The pesticidal composition of claim 10, wherein the transition metal salt comprises nickel, copper, zinc, cadmium, or combinations thereof.

17. The pesticidal composition of claim 16, wherein the transition metal salt comprises zinc.

18. The pesticidal composition of claim 17, wherein the transition metal salt further comprises chloride, sulfate, oxide, hydroxide, hydride, or combinations thereof.

19. The pesticidal composition of claim 18, wherein the transition metal salt comprises zinc chloride, zinc sulfate, or combinations thereof.

20. The pesticidal composition of claim 10, wherein the carrier is Sorbitol, Tween 200, Tween 600, propylene glycol, polyethylene glycol, ethanol methanol, a phosphate ester surfactant, or combinations thereof.

21. The pesticidal composition of claim 10, wherein the carrier is silicon dioxide, zinc oxide, talc, diatomaceous earth, clays, calcium carbonate, wheat flour, powdered nut hulls, or combinations thereof.

22. The pesticidal composition of claim 10, wherein tho composition comprises 0.01 to 25 wt-% organic phenolic compound.

23. The pesticidal composition of claim 22, wherein the composition comprises 0.1 to 15 wt-% organic phenolic compound.

24. The pesticidal composition of claim 23, wherein the composition comprises 0.4 to 13.5 wt-% organic phenolic compound.

25. The pesticidal composition of claim 10, wherein the pesticidal compound is used as an insecticide, miticide, ovicide, fungicide, biocide, insect repellant, or combinations thereof.

* * * * *

UNITED STATES PATENT AND TRADEMARK OFFICE
CERTIFICATE OF CORRECTION

PATENT NO.   : 6,844,396 B2
DATED        : January 18, 2005
INVENTOR(S)  : Ninkov et al.

It is certified that error appears in the above-identified patent and that said Letters Patent is hereby corrected as shown below:

Column 17,
Line 22, should read -- *sis grevei*, and *Lippia graveolens*. --

Column 18,
Line 14, should read -- composition comprises 0.01 to 15 wt-% organic phenolic --

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,844,369 B2
DATED : January 18, 2005
INVENTOR(S) : Ninkov et al.

It is certified that error appears in the above-identified patent and that said Letters Patent is hereby corrected as shown below:

Column 17,
Line 22, should read -- *sis grevei*, and *Lippia graveolens*. --.

Column 18,
Line 14, should read -- composition comprises 0.01 to 15 wt-% organic phenolic --.

Signed and Sealed this

Thirty-first Day of January, 2006

JON W. DUDAS
*Director of the United States Patent and Trademark Office*